(12) United States Patent
Malley et al.

(10) Patent No.: US 8,504,383 B1
(45) Date of Patent: Aug. 6, 2013

(54) METHODS AND SYSTEMS FOR GENERIC OPPORTUNITY SCORING

(75) Inventors: Kenneth Malley, Ho-Ho-Kus, NJ (US); Karnik Patel, Piscataway, NJ (US); Keith J. Bradbury, Blauvelt, NY (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 1047 days.

(21) Appl. No.: 12/362,082

(22) Filed: Jan. 29, 2009

Related U.S. Application Data

(60) Provisional application No. 61/024,960, filed on Jan. 31, 2008.

(51) Int. Cl.
  *G06Q 50/00* (2012.01)
  *G06Q 40/00* (2012.01)

(52) U.S. Cl.
  USPC .................................................. 705/2; 705/4

(58) Field of Classification Search
  USPC ........................................ 705/2, 35
  See application file for complete search history.

(56) References Cited

U.S. PATENT DOCUMENTS

| | | | |
|---|---|---|---|
| 6,219,674 B1 * | 4/2001 | Classen | 1/1 |
| 2002/0042725 A1 * | 4/2002 | Mayaud | 705/2 |
| 2005/0261939 A1 * | 11/2005 | Augspurger et al. | 705/2 |
| 2006/0149784 A1 * | 7/2006 | Tholl et al. | 707/104.1 |
| 2007/0043589 A1 * | 2/2007 | Warren et al. | 705/2 |
| 2007/0299698 A1 * | 12/2007 | Anandarao et al. | 705/4 |

OTHER PUBLICATIONS

Wosinka, Generic dispensing and substitution in mail and retail pharmacies, 2004, Health Affairs 28: W4-409.*

* cited by examiner

*Primary Examiner* — Tran Nguyen
(74) *Attorney, Agent, or Firm* — Husch Blackwell LLP

(57) ABSTRACT

A computer implemented method and/or computer system determines a Generic Opportunity Score (GOS) and/or a generic drug's performance demonstrating how a generic utilization can be better identified and improved relative to the total overall generic opportunity, which can provide savings information relative to a clinically appropriate generic alternative. In some embodiments, the process and/or system determines the GOS as the proportion of generic prescriptions dispensed relative to the maximum number of prescriptions that have a generic equivalent or a clinically-appropriate generic alternative. In some embodiments, the process determines the GOS as the number of generic claims dispensed over the total number of generic claims plus the brand claims that have a generic equivalent or generic alternative. In some embodiments, the data utilized will be provided through a prescription claims database, which can be segmented into three distinct groups: Generic Code Number (GCN), Brand/Generic Code, and Channel, i.e. retail or mail.

7 Claims, 21 Drawing Sheets

---

GENERIC OPPORTUNITY SCORE

THE NEW GENERIC METRIC

---

THE GAP IN MEASURING GENERIC DISPENSING PERFORMANCE BETWEEN GDR AND GSR IS THE VALUE OF GENERIC ALTERNATIVES.

$$\text{GENERIC OPPORTUNITY RATE (GOS)} = \frac{(\text{GENERICS})}{(\text{GENERICS} + \text{BRANDS W/ GENERIC EQUIVALENTS} + \text{BRANDS W/ GENERIC ALTERNATIVES})}$$

- RATE OF GENERIC DISPENSING RELATIVE TO POTENTIAL OPPORTUNITIES FOR USING GENERIC EQUIVALENTS AND GENERIC ALTERNATIVES

GENERIC OPPORTUNITY SCORE

CURRENT METRICS: GSR AND GDR

---

TWO METRICS ARE USED TODAY TO MEASURE GENERIC DISPENSING PERFORMANCE.

$$\text{GENERIC SUBSTITUTION RATE (GSR)} = \frac{(\text{GENERICS})}{(\text{GENERICS} + \text{BRANDS W/ GENERIC EQUIVALENTS})}$$

- THE RATE OF GENERIC DISPENSING RELATIVE TO TOTAL DISPENSING $$\text{GENERIC DISPENSING RATE (GDR)} = \frac{(\text{GENERICS})}{(\text{GENERICS} + \text{ALL BRANDS})}$$

- THE RATE OF GENERIC DISPENSING RELATIVE TO OPPORTUNITIES FOR USING GENERIC EQUIVALENTS

FIG. 1A

GENERIC OPPORTUNITY SCORE

THE NEW GENERIC METRIC

THE GAP IN MEASURING GENERIC DISPENSING PERFORMANCE BETWEEN GDR AND GSR IS THE VALUE OF GENERIC ALTERNATIVES.

$$\text{GENERIC OPPORTUNITY RATE (GOS)} = \frac{\text{(GENERICS)}}{\text{(GENERICS + BRANDS W/ GENERIC EQUIVALENTS + BRANDS W/ GENERIC ALTERNATIVES)}}$$

- RATE OF GENERIC DISPENSING RELATIVE TO POTENTIAL OPPORTUNITIES FOR USING GENERIC EQUIVALENTS AND GENERIC ALTERNATIVES

FIG. 1B

COMPARISON OF GENERIC OPPORTUNITY SCORE TO GSR AND GDR

| | GSR | GDR | GOS |
|---|---|---|---|
| MEASURE GENERIC UTILIZATION RELATIVE TO GENERIC EQUIVALENT OPPORTUNITY | ✓ | | |
| MEASURES USE OF GENERIC ALTERNATIVES AS WELL AS EQUIVALENTS | | ✓ | |
| MEASURES GENERIC UTILIZATION AGAINST ACTUAL POTENTIAL FOR UTILIZATION OF GENERIC EQUIVALENTS AND ALTERNATIVES | | | ✓ |
| CLINICALLY BASED MEASURE OF REAL OPPORTUNITY TO USE GENERIC ALTERNATIVES | | | ✓ |

FIG. 1C

GENERIC OPPORTUNITY SCORE

THE GENERIC OPPORTUNITY SCORE (GOS), REVEALS TO PBMS THEIR TOTAL POTENTIAL OPPORTUNITY FOR USING GENERICS, BOTH AS GENERIC EQUIVALENTS AND GENERICS ALTERNATIVES.

GOS ALLOWS:

- A CLIENT-SPECIFIC ASSESSMENT OF CURRENT GENERICS PERFORMANCE AND POTENTIAL GENERICS UTILIZATION
- CURRENT PERFORMANCE AND OPPORTUNITY TO TIE TO TOTAL POTENTIAL SAVINGS
- PRIORITIZATION OF OPPORTUNITIES BY THERAPEUTIC CLASS
- CREATION OF TAILORED GENERIC STRATEGIES BASED ON IDENTIFIED POTENTIAL OPPORTUNITIES

FIG. 1E

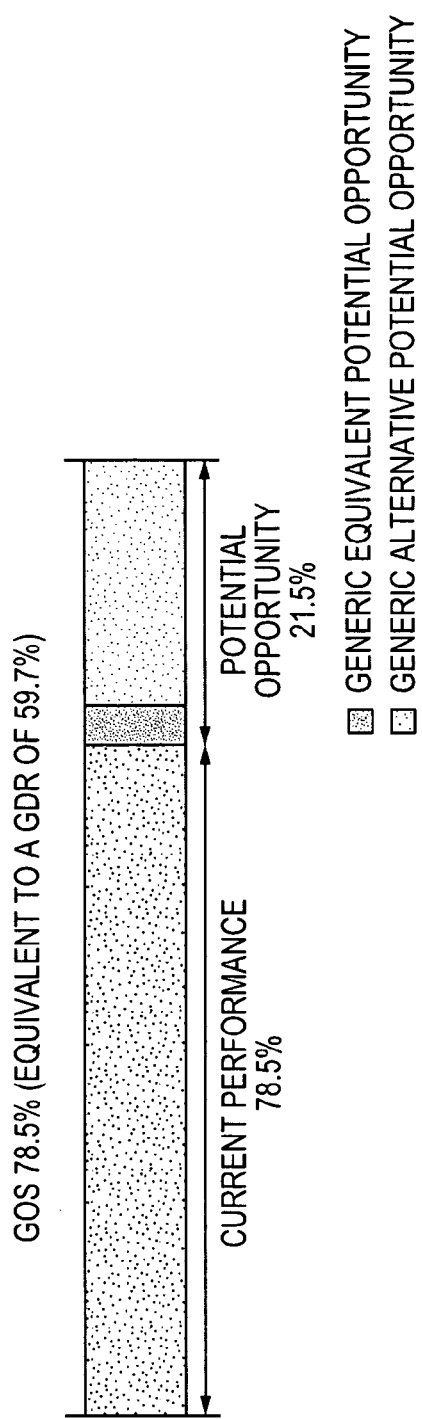

IDENTIFYING GENERIC ALTERNATIVE OPPORTUNITY
THERAPEUTIC ALTERNATIVE DATABASE

COMPREHENSIVE LISTING OF SINGLE-SOURCE BRAND MEDICATIONS WITH GENERIC ALTERNATIVES

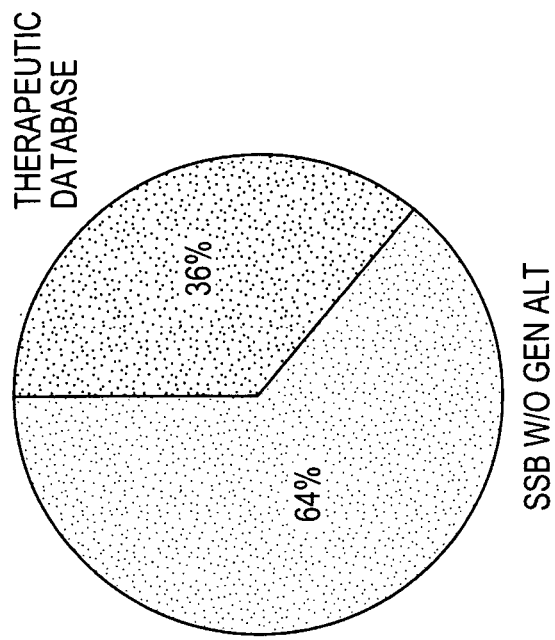

SINGLE-SOURCE BRAND % OF DRUGS

THERAPEUTIC DATABASE

36%

64%

SSB W/O GEN ALT

GENERIC EQUIVALENTS

- DMAA DEVELOPED GENERIC ALTERNATIVE DATABASE
  - DRUG PAIRS ARE BASED ON AVAILABLE CLINICAL EVIDENCE AND RECOMMENDATIONS OF P&T COMMITTEE
  - ALL PAIRS ARE ASSIGNED AN EXPECTED SUCCESS RATE OF CONVERSION TO THE GENERIC ALTERNATIVES AS DETERMINED BY CLINICAL EVIDENCE, MEDICAL NECESSITY, AND FINANCIAL CONSIDERATIONS*

*FINANCIAL CONSIDERATIONS ASSUME MEMBER PAYS 100%, WITH NO COVERAGE REVIEW

FIG. 4B

GENERIC OPPORTUNITY:
WHAT IS IT?

| GENERIC OPPORTUNITY RATE |

- ESTIMATES THE PERCENTAGE OF SSB CLAIMS THAT COULD BE REPLACED BY A GENERIC MEDICATION IF GENERICS WERE PRESCRIBED WHENEVER CLINICALLY POSSIBLE.

- DRUG-SPECIFIC
  - RATE MAY VARY BY DOSAGE STRENGTH/DOSAGE-FORM LEVEL

FIG. 4F

METHODS AND SYSTEMS FOR GENERIC OPPORTUNITY SCORING

RELATED APPLICATIONS

Pursuant to 35 U.S.C. §119, this application claims benefit to U.S. Application No. 61/024,960, filed on Jan. 31, 2008, incorporated herein by reference in its entirety.

FIELD OF THE INVENTION

This invention generally relates to determining the available opportunity in pharmaceutical marketplace to increase the usage of generics, thereby lowering overall costs to the payer and consumer. The invention also relates to determining the available opportunity in the pharmaceutical marketplace to increase the usage of generics while also carefully considering the possible health impact on a consumer.

In accordance with at least one embodiment of the invention, a pharmaceutical benefits management system is able to administer a pharmaceutical benefits program more cost effectively, thereby lowering the cost to consumers to be a subscriber of the pharmaceutical benefits program and/or lower the costs of payors in providing benefits to members in their plan.

BACKGROUND OF THE INVENTION

Generic drugs can be classified as being generic equivalents and/or generic alternatives to brand medications. Generic equivalents are drugs produced, typically after the expiration of patent rights, which contain the same active ingredients as the original brand name drug. That is, drugs approved by the Food and Drug Administration (FDA) as generic equivalents are considered the bioequivalent to the brand name counterpart with respect to, inter alia, pharmacokinetic and pharmacodynamic properties. Typically, generic equivalents are identical in dose, strength, route of administration, safety, efficacy, and intended use.

Generic alternatives work similar to a brand drug and can be used to treat the same condition. However, the chemicals in a generic alternative can differ from the brand drug or its generic equivalent. Both generic equivalents and generic alternatives are typically less expensive than the original brand name product. Thus, generic drugs can provide patients with a less expensive option to achieve similar therapeutic results.

Today, referring to FIG. 1A, the Pharmacy Benefits Managers (PBM) industry primarily measures generics utilization by two metrics—Generic Dispensing Rate (GDR) and Generic Substitution Rate (GSR). GDR shows generic dispensing as a proportion of total prescription (Rx) dispensing. GDR demonstrates the overall level of generic dispensing; however, it does not provide users with insight into the potential remaining opportunity or upper limit of generic dispensing. The broad nature of GDR is due to the fact that the calculation includes all medications, including those medications that may not have any available generic equivalent or alternatives. GSR is the percentage of multi-source claims (i.e., multi-source brands plus generics) dispensed as generics. GSR is a highly focused measure of the success in substituting generic equivalents when one is available, but excludes any opportunity for use of clinically appropriate generic alternatives. In fact, with the PBM industry's success in adopting generic equivalents, GSR has reached significant saturation levels (e.g., in the 90-97% range for generic equivalents) that translate to minimal growth opportunities for users.

While GDR and GSR serve as straight forward measures of generic dispensing and utilization, we have identified at least two important limitations. First, GDR and GSR have difficulty in projecting future performance due to their construct to measure current versus past performance. Second, GDR and GSR are not able to portray the total potential generic opportunity and the importance of generic alternatives in producing savings. A need exists to overcome, inter alia, the aforementioned deficiencies, as well as others described below.

SUMMARY OF INVENTION

It is therefore a feature and advantage of the present invention in some of the embodiments in providing a method and/or system to identify future potential generic equivalent or alternative opportunity. It is a further feature and advantage of the present invention to not only demonstrate the total potential generic equivalent or alternative opportunity, but also the inherent savings opportunity as a result.

It is another optional and/or alternative feature and advantage of the present invention in providing a method and/or system to provide to a client a personalized assessment of potential generics utilization, allow clients to tie current performance and future opportunity to potential savings, allow clients to prioritize high-value opportunities by therapeutic class and tailor solutions based on the assessment.

It is another optional and/or alternative feature and advantage of the present invention in providing a method and/or system to provide to a user a letter, an email or automated message informing user of assessed generic alternative recommendations.

It is another optional and/or alternative feature and advantage of the present invention in providing a method and/or system to provide the user with separate generic equivalent opportunity and generic alternative opportunity and basing the total generic opportunity on the generic equivalent and alternative opportunities.

It is another optional and/or alternative feature and advantage of the present invention in providing a method and/or system to provide the user with generic opportunity at any detail level deemed suitable by the user.

It is another optional and/or alternative feature and advantage of the present invention in providing a method and/or system to provide the user with totals of generics dispensed, generic equivalent opportunities and generic alternative opportunities.

It is another optional and/or alternative feature and advantage of the present invention in providing a method and/or system to provide the user with the ability to determine the generic opportunity score based on predetermined criteria.

There has thus been outlined, rather broadly, the more important features of the invention and several, but not all, embodiments in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The above and other objects and advantages of the disclosed subject matter will be apparent upon consideration of the following detailed description, taken in conjunction with accompanying drawings, in which like reference characters refer to like parts throughout, and in which:

FIG. 1A illustratively depicts two metrics (i.e., GSR and GDR) used to measure generic dispensing performance in accordance with some embodiments of the disclosed subject matter;

FIG. 1B illustratively depicts the metric (i.e., GOS) in accordance with some embodiments of the disclosed subject matter;

FIG. 1C illustratively depicts a comparison of GOS to GDR and GSR with various types of measurement factors for each metric in accordance with some embodiments of the disclosed subject matter;

FIG. 1E illustratively depicts the overall value provided by the Generic Opportunity Score calculation;

FIG. 3 illustrates the knowledge generated via a GOS diagnostic tool, the current performance of GOS, Generic Equivalent Opportunity (GEO), and Generic Alternative Opportunity (GAO), and the identified opportunity to improve GOS across generic equivalents and alternatives in accordance with some embodiments of the disclosed subject matter;

FIG. 4B illustratively displays at least some of the generic alternative criteria for a therapeutic alternative database in accordance with some embodiments of the disclosed subject matter;

FIG. 4F illustratively displays the Generic Opportunity Rate and factors included in such determination;

DETAILED DESCRIPTION

Figure 1D:
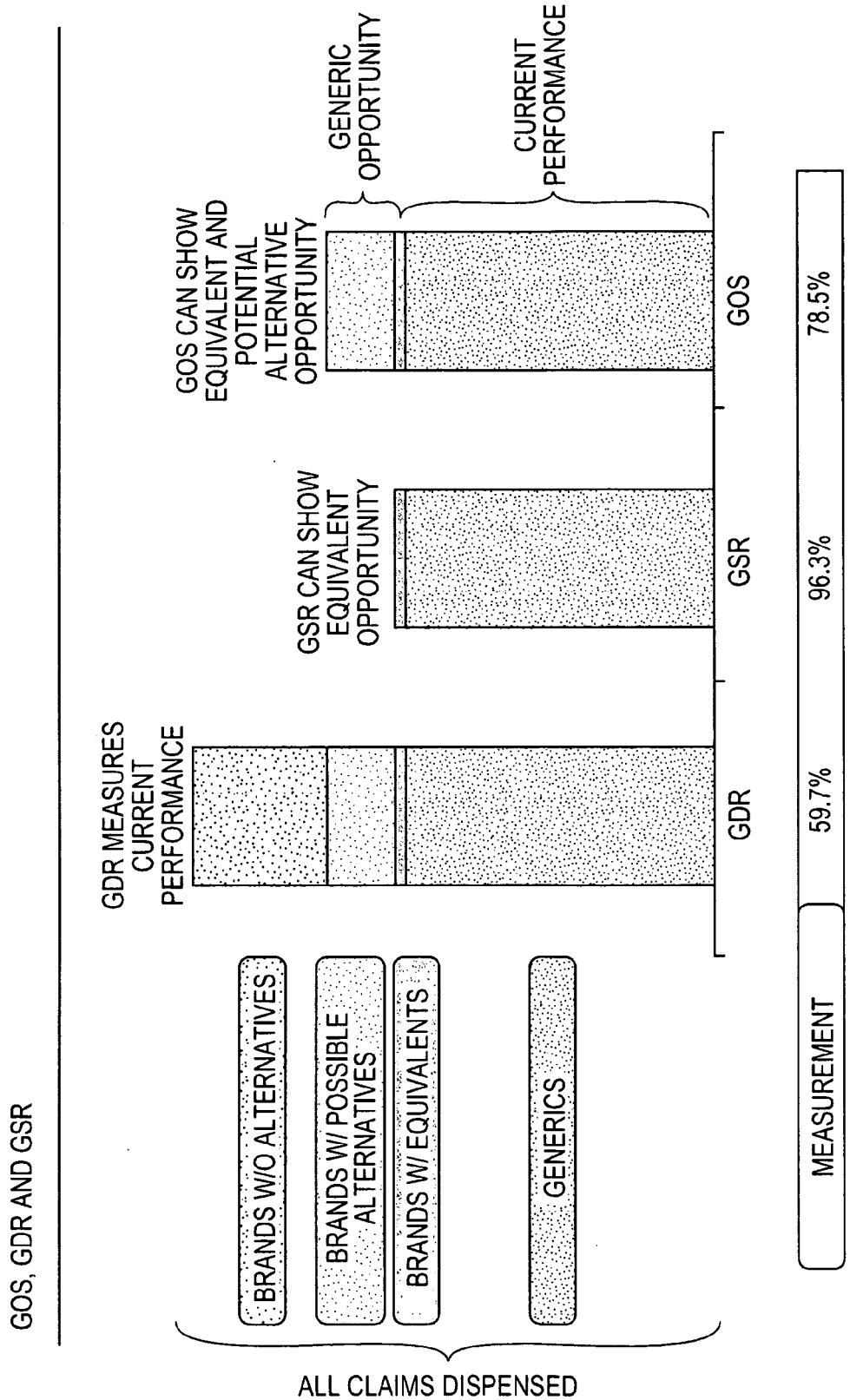
FIG. 1D illustratively depicts a graphical comparison of the three generic metrics in accordance with some embodiments of the disclosed subject matter.

The following description includes many specific details. The inclusion of such details is for the purpose of illustration only and should not be understood to limit the invention. Moreover, certain features which are well known in the art are not described in detail in order to avoid complication of the subject matter of the present invention. In addition, it will be understood that features in one embodiment may be combined with features in other embodiments of the invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. Other alterations or modifications of the above processes are also contemplated. For example, further insubstantial approximations of the process and/or algorithms are also considered within the scope of the processes described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

In some embodiments, a Generic Opportunity Score (GOS) can be a generics performance metric that can show how generic utilization can be better identified and improved relative to the total overall generic opportunity. Further, in some embodiments, GOS can be a diagnostic tool, based on modeling and/or calculated by using clinically-based methodologies across a user's prescription claims databases to identify the percentage of generic claims that could have been potentially captured if all clinically appropriate generic equivalent and alternative substitutions were made. Further still, in some embodiments, GOS can, inter alia, provide to a user a personalized assessment of potential generics utilization, allow users to tie performance and opportunity to potential savings, provide prioritization of high-value opportunities by therapeutic class, and provide tailored solutions based on value assessment.

In some embodiments, referring to FIG. 1B, GOS can be defined as the proportion of generic prescriptions dispensed relative to the maximum number of prescriptions that have a generic equivalent or a clinically-appropriate generic alternative. For example, the formula or process to compute GOS can be expressed as the number of generic claims dispensed over the total number of generic claims plus the brand claims that have a generic equivalent or generic alternative. Further, GOS can optionally include acute and maintenance medications.

FIG. 1C illustratively depicts a comparison of GOS to GDR and GSR with various types of measurement factors for each metric. As displayed, in some embodiments, GOS indicates to a user the total generic opportunity available because it accounts for the proportion of generic prescriptions dispensed relative to the maximum number of prescriptions that have a generic equivalent or a clinically appropriate generic alternative. Unlike GDR, GOS and GSR can measure generic utilization relative to generic equivalent opportunity. Unlike GSR, GOS and GDR can measure use of generic alternatives as well as equivalents. Unlike GSR and GDR, GOS can provide a clinically based measure of real potential opportunity to use generic alternatives. Unlike GSR and GDR, GOS can measure generic utilization against actual potential for utilization of generic equivalents and alternatives.

FIG. 1D. illustratively depicts a graphical comparison of the three generic metrics. As displayed, each of GDR, GOS, and GSR can represent generics performance relative to a certain set of claims. For example, GDR measures generic performance relative to all claims, at 59.3% generics, whereas GOS measures generic performance relative to all claims with generic equivalent and generic alternative potential, at 79.3% generics, and GSR represents generic performance relative to all claims that have a generic equivalent, at 96.6% generics. Further, each of GDR, GOS, and GSR can include the same volume of generics, however when measured against its specific opportunity can have different values. Further still, GDR and GOS can include brands with alternatives and GDR can include brands without alternatives. Further, as displayed, GOS can measure all potential actionable opportunity. GSR can measure only equivalent opportunity.

Furthermore, the GOS can provide an assessment of current generics performance, as well as potential utilization. The assessment of the current generics performance assists in determining the potential savings of moving to a clinically appropriate generic alternative. This allows a PBM, for example, the opportunity to tailor generic strategy policy based on a GOS assessment. See FIG. 1E.

The GOS assessment is distinguishable from GDR, in that GDR is too broad to provide a one-to-one drug comparison. Alternatively, GSR, which can be used in a one-to-one comparison fashion, is limited as GSR rates are typically greater than 90% and payers may have members pay the difference type plans. This results in a limited savings opportunity.

Figure 2:
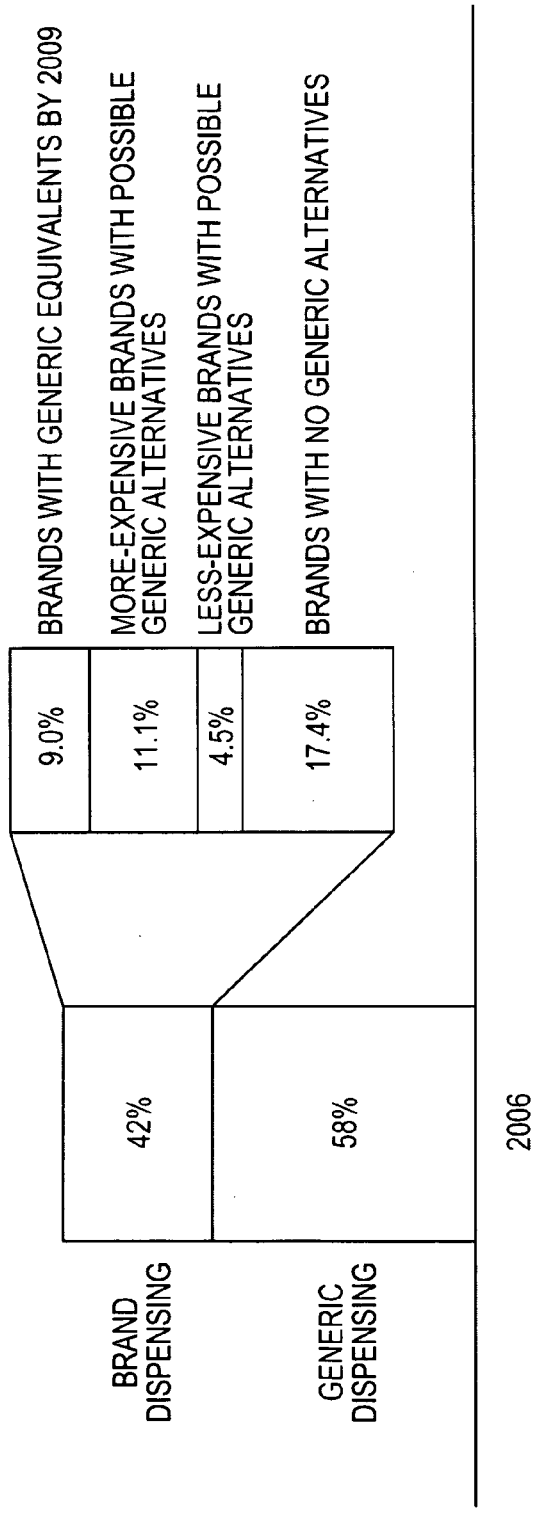
FIG. 2 illustratively depicts the potential opportunity for brand-to-generic conversions for a three year period (e.g., 2006 to 2009) in accordance with some embodiments of the disclosed subject matter.

FIG. 2 illustratively depicts the potential savings from brand-to-generic conversions for a three year period (e.g., 2006 to 2009). The model can be based on information, analysis, and dispensing rates for a PBM corporation (e.g., Medco). For example, out of all drugs dispensed 58% can be from generic dispensing while 42% can be from brand dispensing. Within this 42% of brand dispensing an opportunity can exist to dispense generics. As shown, there can be an 11.1% savings opportunity associated with conversions from higher cost brands to generic alternatives. Further, a 9% opportunity can exist for brands which will have generic equivalents by 2009, and 4.5% opportunity can exist for less-expensive brands with generic alternatives.

In some embodiments, GOS reflects how much of the opportunity to use generics can potentially be achieved within a user's member base. FIG. 3 illustrates the knowledge generated via a GOS diagnostic tool (e.g., any tool used to better understand the GOS) indicating the current performance of GOS and GDR and the identified opportunity to improve GOS and GDR across generic equivalents and alternatives. For example, for a PBM corporation (e.g., Medco) the GOS can be 79.7% equating to a GDR of 60.4%. The difference between GOS and GDR can in some instances be from the fact that generic dispensing in GOS can be measured only relative to the opportunity of utilizing a generic equivalent or alternative. Of the remaining 20.3% opportunity, only about 2.8 percent can be gained by increasing the use of generic equivalents where multi-source brand drugs are being used today. The remaining opportunity can be based on members using generic alternatives for the drugs they are using today.

In some embodiments, GOS can provide users with the ability to have a practical and actionable measure of potential opportunity to gain incremental value from generics, down to the individual drug level. In some embodiments, users can see every prescription that could have been filled with a generic equivalent or clinically-appropriate generic alternative and calculate how many of those opportunities can be converted, leading to an estimate of unrealized incremental potential cost savings.

In some embodiments, users can assess their opportunities for improved generics utilization and the associated areas of additional savings. Further, drug providers (e.g., pharmacy benefit managers) can indicate to their users where and how to achieve the savings potential through plan design approaches (e.g., modifying the users plan design to increase savings, and influence member behavior), formulary strategies (e.g., substituting, replacing, or suggesting alternative brand or generic formulary drugs to increase plan savings, and rebates), and enrollment options in various programs designed to increase generics utilization (e.g., agreeing that users may participate in communication and/or other programs to influence drug selection towards generic choices). The amount of incremental savings may vary by user, but many can have significant savings opportunities resulting in lower costs while providing clinically based therapy alternatives.

Figure 4A:
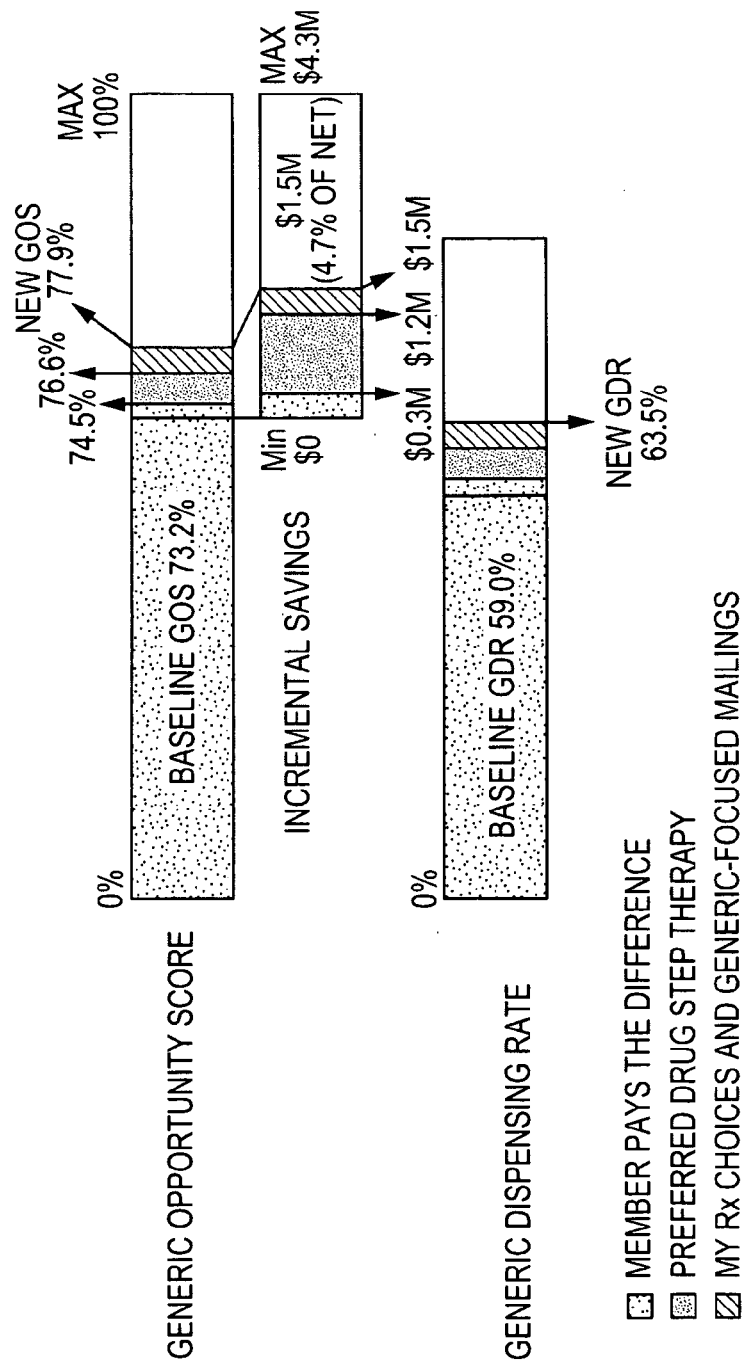
FIG. 4A illustratively displays at least some of the advantages of the GOS for a national account user, and how GOS can be tied back GDR in accordance with some embodiments of the disclosed subject matter.

Referring to FIG. 4A, in some embodiments, at least some of the advantages of the GOS can be depicted for an average client. For example, in some embodiments, the GOS analysis provides the user with information previously unavailable and specific approaches to attain increased GOS, GDR, and target savings. For example, potential savings opportunity for equivalents and alternatives can range up to $1,500,000.

In some embodiments, GOS includes a therapeutic alternative database. The therapeutic alternative database can be a central repository for identified generically-available therapeutic alternatives for commonly prescribed brand-name drugs. In some embodiments, the therapeutic alternative database can be a comprehensive listing based on a prescription claim databases. For example, a database with 600 drugs and their approximately 1,400 available dosage strengths and dosage forms can represent 95% to 98% of all branded prescription drug claims volume.

Further, referring to FIG. 4B, the therapeutic alternative database can include drug pairs, which are determined by a predetermined criteria and conversion rate. For example, generic alternative criteria can include, but is not limited to, a comprehensive listing of generically available therapeutic alternatives for commonly prescribed medications; available evidence and recommendation from a committee; and expected rate of conversion can be accounted for based on both clinical evidence and financial considerations. Further, for example, a single source brand could include a percentage that represents the likelihood a single source brand could be used as a generic alternative (e.g., 64%) and a percentage that represents the likelihood a single source brand could not be used as a generic alternative (e.g., 36%).

In some embodiments, the therapeutic alternative database can include a list of drugs and dosage strengths and a result of either no generic alternatives or the alternatives identified at the dosage strength and dosage form level. In some embodiments, the generically available alternative can be based on at least one of a defined population of single-source brand name drugs that have clinically appropriate generic therapeutic alternatives and population developed from a prescription databases, for example, with the 600 single-source brand-name drugs accounting for 95-98% of all branded prescription drug claims volume and a definition of qualifying generic alternatives.

In some embodiments, the definition of generic alternatives includes, but is not limited to, multi-source drugs within the same or closely related pharmacologic and/or chemical category as the index drug, for example ACE inhibitors and Agiotensin II receptor blockers that shared the same or similar FDA labeled indications, relative potency, safety and efficacy, and dosage forms based on available evidence, and/or the past recommendations of the independent committee (e.g., Pharmacy & Therapeutics (P&T) Committee) brought together by, for example, a PBM corporation. In other words, generic drug alternatives can be viewed as generally interchangeable with brand name drugs based on, inter alia, the independent committee's analysis.

In some embodiments, the definition of generic alternatives includes, but is not limited to, multi-source drugs in different pharmacologic or chemical classes that also shared the same or similar labeled indications, dosage forms, safety and efficacy and relative potency based on available evidence, and/or past recommendations from an independent committee.

In some embodiments, the definition of generic alternatives includes, but is not limited to, multi-source drugs that could serve as alternatives to brand name drugs with respect to the drug formularies that have been developed with the advice and/or analysis of the independent committee.

Figure 4C:
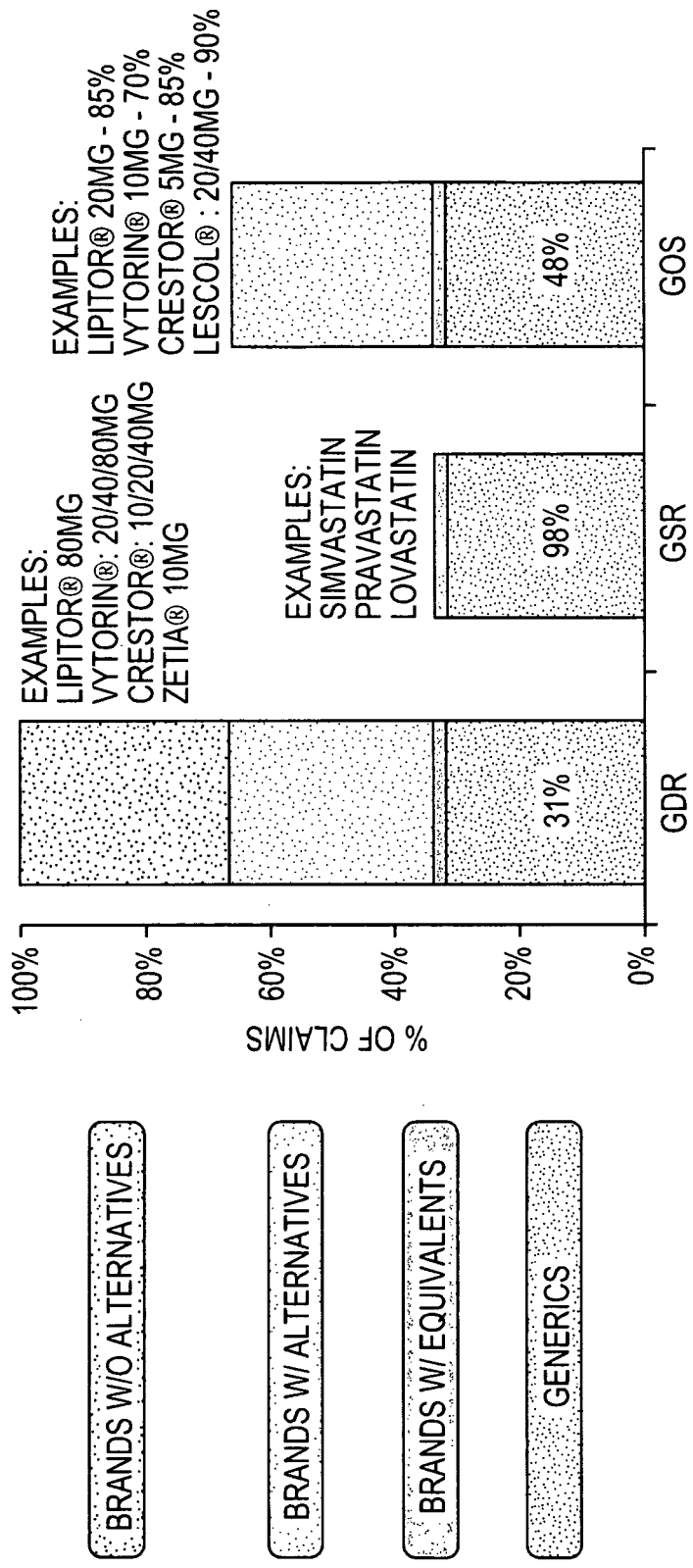
FIG. 4C illustratively displays an example of a therapeutic alternative database for lipid lowering agents in accordance with some embodiments of the disclosed subject matter.

Referring to FIG. 4C an example of a therapeutic alternative database for lipid lowering agents is illustratively displayed. For example, for lipid lowering agents the therapeutic database can include generics (e.g., simvastatin, pravastatin, and lovastatin), brands with equivalents, brands with alternatives (e.g., Lipitor® 20 mg, Vytorin® 10 mg, Crestor® 5 mg, and Lescol® 20/40 mg), and brands without alternatives (e.g., Lipitor® 80 mg, Vytorin® 20/40/80 mg, Crestor® Oct. 20, 1940 mg, and Zetia® 10 mg). Further, as displayed, the percentage of generics calculated for GDR is 31%, GOS is 48%, and GSR is 98%.

Figure 4D:
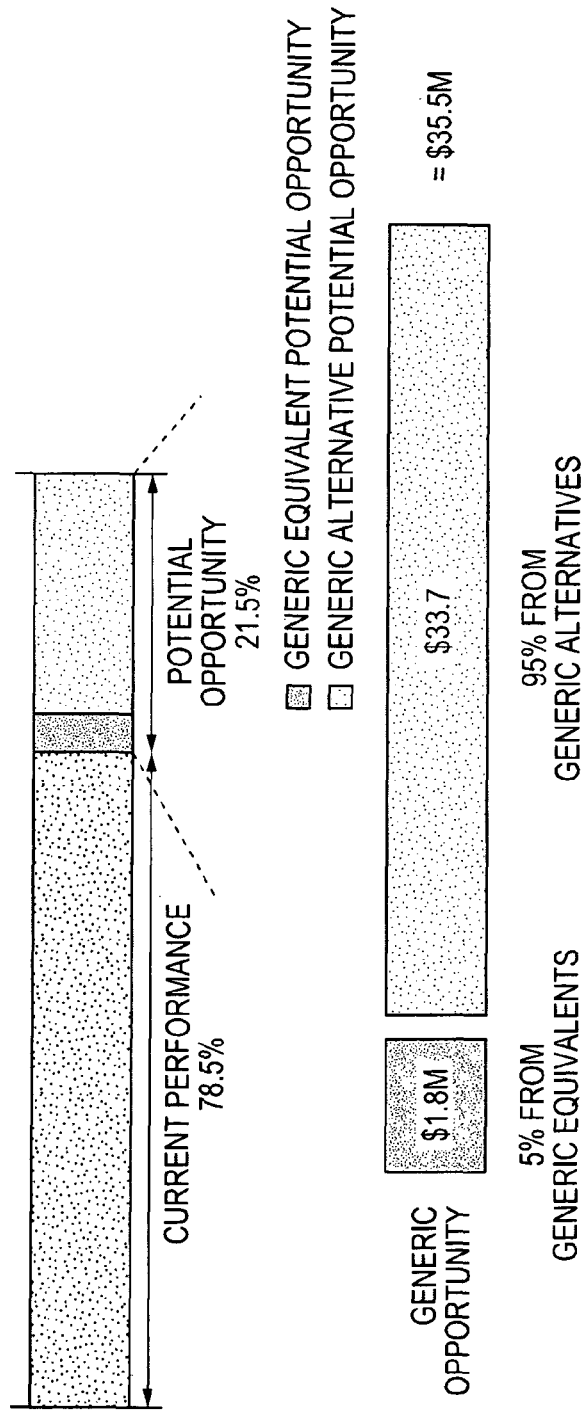
FIG. 4D illustratively displays a user example for GOS in accordance with some embodiments of the disclosed subject matter.

Referring to FIG. 4D, a user example for GOS is illustratively displayed in accordance with some embodiments. As displayed, the GOS for the user is 78.5% (equivalent to a GDR of 59.7%). This indicates a 19.6% opportunity (i.e., generic equivalent opportunity and generic alternative opportunity) for the user. The 21.5% opportunity includes 5% from generic equivalents ($1.8 Million in incremental savings) and 95% from generic alternatives ($33.7 Million in incremental savings) indicating a total incremental savings of $35.5 Million.

Figure 4E:
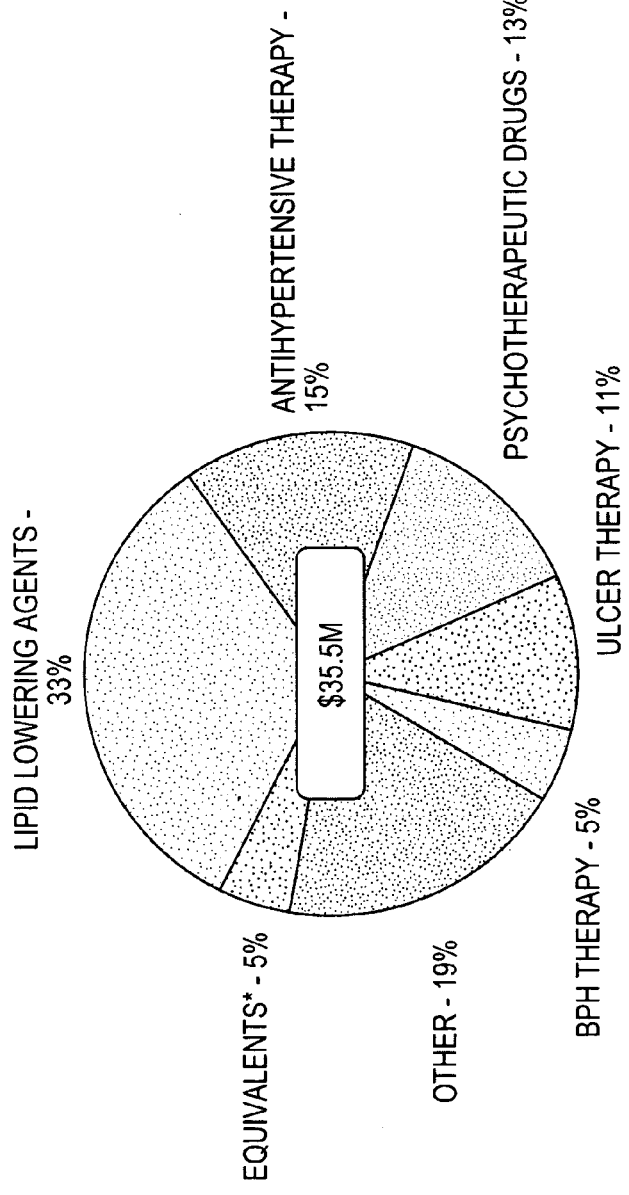
FIG. 4E illustratively displays at least some of the categories for opportunity in generic savings for a user example in accordance with some embodiments of the disclosed subject matter.

Referring to FIG. 4E, the $35.5 Million (or 19.6% opportunity) in generic savings can be from a plurality of categories. The categories can include, but are not limited to, lipid-lowering agents; antihypertensives, psychotherapeutics, ulcer therapy, BPH therapy, and any other category deemed suitable. Further, each of the categories can include a dollar amount totaling to $35.5 Million.

In some embodiments, after the working definition of therapeutic alternatives is determined, a two step process can be used to develop an allocation list (e.g., a list containing alternative generic medications to branded product and the probable patient conversion rate based on the clinically required use of the branded product, etc.). At step 1, drugs can be identified without generically available alternatives. In some instances, two categories may be designated for this step: protein-based drugs or biologics and non-protein based drugs. Protein-based biologics can be defined as drugs which the FDA does not yet have a process for approving generic equivalents. This includes drugs that may not appear to have any generically available alternatives. Non-protein based drugs can belong to unique pharmacologic and chemical classes (e.g., triptans or bisphosphonates) that may not have available generics in the same or even related classes with similar labeled indications. Safety and efficacy can be included as criteria in this group.

In some embodiments, at step 2, generically available drug(s) at a dosage strength level that could serve as a possible therapeutic alternative to each of the single source brand drugs can be assigned. If more than one drug is available, the drug with the greater market share or prevalence of use may be selected. Dosage strength of the generic alternative can be based on a range of approved daily dosages for the index drug and its generic alternative with interpolation where needed. Assignments can be made, for example, for costing purposes and may not be intended to be precise clinical matches. The process can be continued until all drugs are assigned as alternatives or no alternative.

Figure 4G:
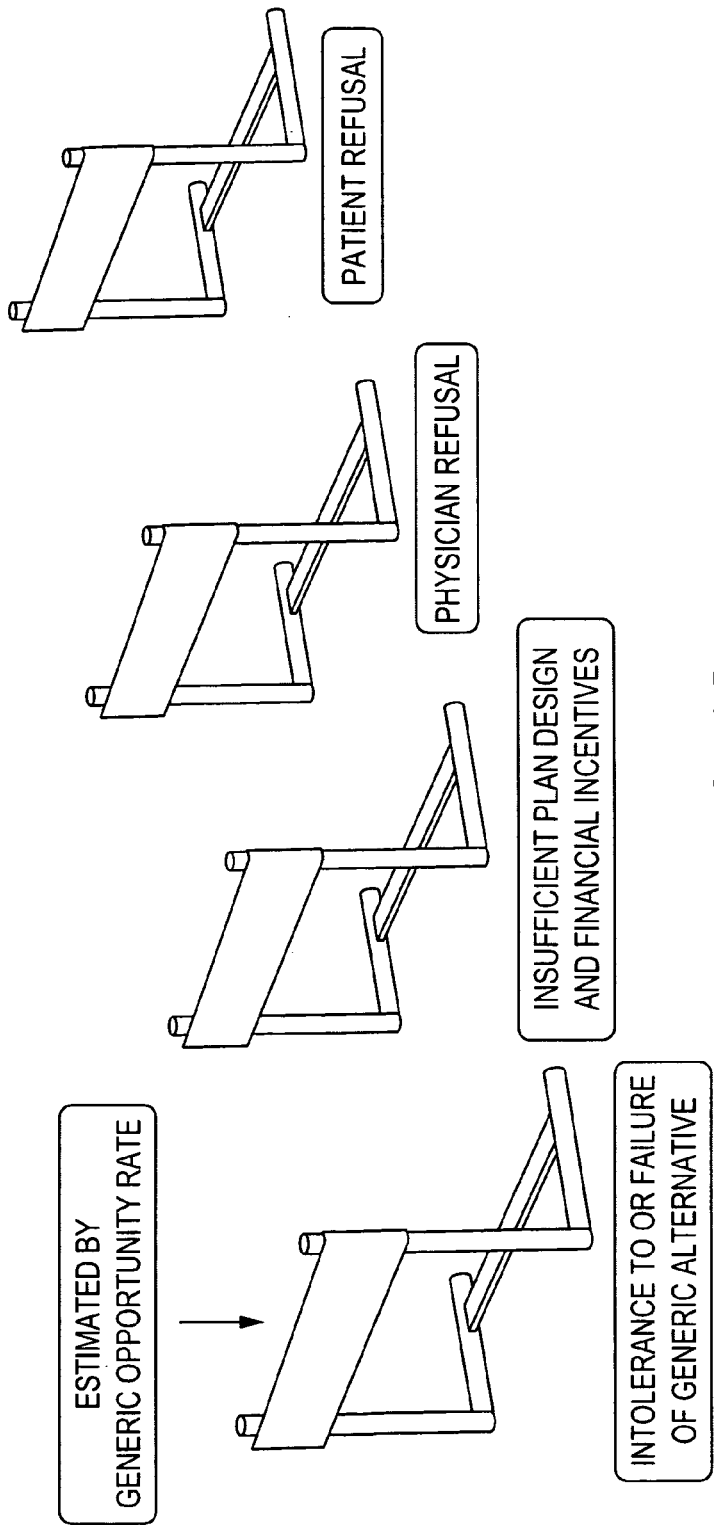
FIG. 4G illustratively depicts considerations included in the calculation of the Generic Opportunity Rate.

In some embodiments, after the generic alternatives have been assigned, where applicable, one of the next steps can be to determine the generic opportunity rate, an estimate of the percentage of single source brand (SSB) claims, i.e., claims that do not have a generic equivalent, that could be replaced by a generic medication if generics were prescribed whenever clinically possible (rate is drug specific and may vary by dosage strength and form) as shown in FIG. 4F. Alternatively, other factors, e.g., intolerance to or failure of generic alternatives, insufficient plan design and financial incentives, physician refusal to prescribe the generic drug, patient refusal to accept the generic drug, etc., may impact the Generic Opportunity Rate. See FIG. 4G. These decisions can be made by the patient, physician, or any other group, individual, or artificial intelligence deemed suitable. In some instances, incentives or restrictions on access to the brand(s) that would be implemented by the plan may need to be considered. For example, a plan could be implemented where the brand is not covered by the plan, but the generically available alternative could be covered.

In some embodiments, criteria can be used for assigning the likely generic opportunity rates. For example, some criteria that can be used includes, but is not limited to, the clinical similarity of the index drug and the alternative in terms of pharmacology, chemistry, safety and efficacy, labeled indications; the typical duration of efficacy for drug(s) involved; the overall probability and reliability of a beneficial response to the drugs in the class; the total cost for the brand name medication that the patients would have to pay themselves; opinions/analysis of several members of the department of medical affairs at a PBM corporation can be included for each drug pair in making the final determination of conversion rates; and where a disparity in opinions/analysis existed, these can be adjudicated and a consensus opinion/analysis can be established.

In some embodiments, by defining the scenario with the patient paying the entire cost of the brand drug or choosing to use the generic alternative, the likelihood of a true clinical need for the brand(s) can be the principle determinant for the estimates of generic opportunity rates instead of a patient's personal preference for the brand. For example, the generic opportunity rates can be on the order of 90% to 95% assuming brands that are an A-rated generic (i.e., medication the FDA has determined is equivalent to the brand name product in safety and effectiveness) exists. Where the generic alternative is in the same pharmacologic class of drugs as the brand (e.g., a different ACE inhibitor) a generic opportunity rate in the range of 80% to 90% can be assumed. Whenever a drug in a different class is the alternative, a lower rate of generic opportunity can be assumed, for example 50% to 60% if the pharmacologic classes are similar, but not the same. In cases where the condition being treated involves the use of several drugs at once (e.g. diabetes), a lower rate of generic opportunity (e.g. 20% to 25%) may be estimated based on the likelihood that the alternative may already have been used. Consistency can be maintained when determining conversion rates for similar circumstances, for example, the same circumstances (e.g., one brand Proton Pump Inhibitor (PPI) to a generic PPI) were treated similarly.

In some embodiments, the GOS can be a relative measure of the total generic opportunity within a user's prescription claims database. The process for calculating GOS can require defined data sets for total generic prescriptions dispensed, total generic equivalents dispensed, and total generic alternatives dispensed. After collecting the claims data, the data within defined parameters can be organized resulting in three groups from which to sort and create the total generic opportunities that can be the factors to compute GOS.

Figure 5:
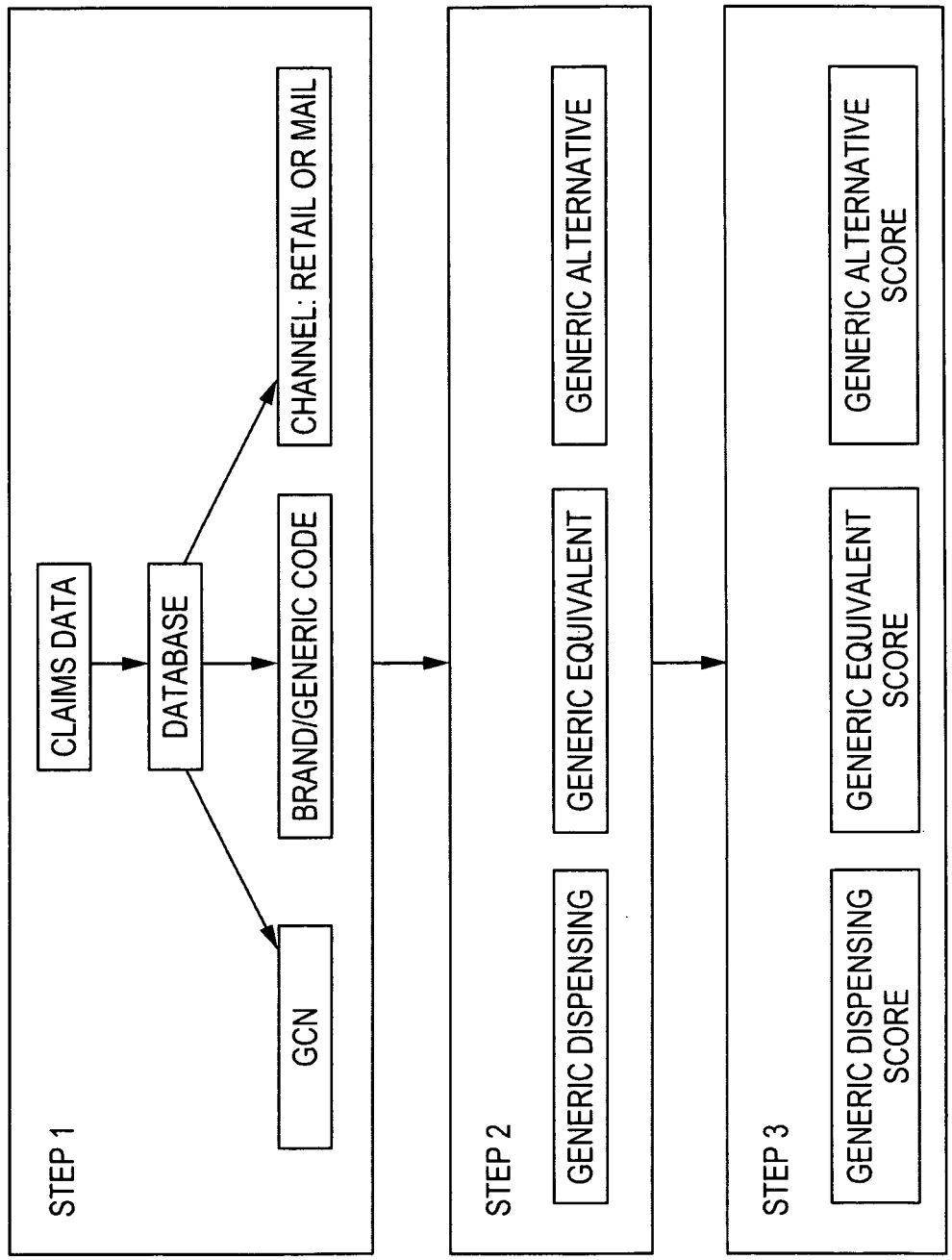
FIG. 5 illustratively displays a process map for collecting the data, creating the data sets, assigning codes, defining the final discreet generic data sets from which the GOS, GEO, and GAO calculations are derived in accordance with some embodiments of the disclosed subject matter.

Referring to FIG. 5, a process map for collecting the data, creating the data sets, assigning codes, and defining the final discrete generic data sets from which the GOS calculations are derived is illustratively displayed. At step 1, claims data for a user or representative sample can be imported into a database and segmented into three distinct groups: Generic Code Number (GCN), Brand/Generic Code, and Channel: Retail or Mail. GCN can be a unique five character number representing generic formulation. Further, GCN can be specific to generic ingredient combination, route, dosage form and drug strength. Brand/Generic Code can indicate if the dispensed drug is a brand or generic based on one of three types: a single-source brand, a multi-source brand, and a generic. Channel: Retail or Mail can be the sum totals accumulated for both channel types across various parameters such as, but not limited to: sum claims, sum days, sum quantity, sum average wholesale price (AWP), sum ingredient cost, sum gross cost, sum patient payment, and sum net cost.

Further, in some embodiments, at step 2 three discrete generic data sets can be created: Generics Dispensed, Generic Equivalents, and Generic Alternatives. Generics Dispensed can be the sum claims for all GCNs by channel with either a Brand or Generic, designated by, for example, a code of (G). Generic Equivalents can be sum claims for all GCNs by channel with either a Brand or Generic, designated by, for example, a code of (B) for multi-source brands. Generic Alternatives can be sum claims of only the GCNs indicated on the therapeutic alternative database as having a generic alternative. These can then be grouped by channel and designated as a Brand or Generic code of, for example, (A) for single-source brands. In alternative embodiments, one or more of the three discrete generic data sets, other data described herein relating to the GOS and/or combinations thereof, may be used.

Further still, in some embodiments, at step 3 the GOS can be calculated. The GOS formula can be represented as the Generics Dispensed over the Sum of Generics Dispensed, Brands with Generic Equivalents, and Brands with Generic Alternatives). The Generic Equivalent Opportunity (GEO) score formula can be represented as the Generic Equivalents over the sum of Generics Dispensed, Brands with Generic Equivalents, and Brands with Generic Alternatives. The Generic Alternative Opportunity (GAO) score formula can be represented as the Generic Alternatives over the sum of Generics Dispensed, Brands with Generic Equivalents, and Brands with Generic Alternatives. GEO can represent the portion of opportunity for which a therapeutic equivalent exists for a branded product, for example, as depicted in FIG. 3. GAO can represent the portion of opportunity for which a therapeutic alternative exists for a branded product, for example, as depicted in FIG. 3.

GOS can be defined as the success rate of generic dispensing when a generic equivalent or clinically-appropriate generic alternative is available. 100 minus GOS can represent the remaining opportunity to increase generics utilization where a generic equivalent and/or a clinically appropriate generic alternative are available.

Figure 6:
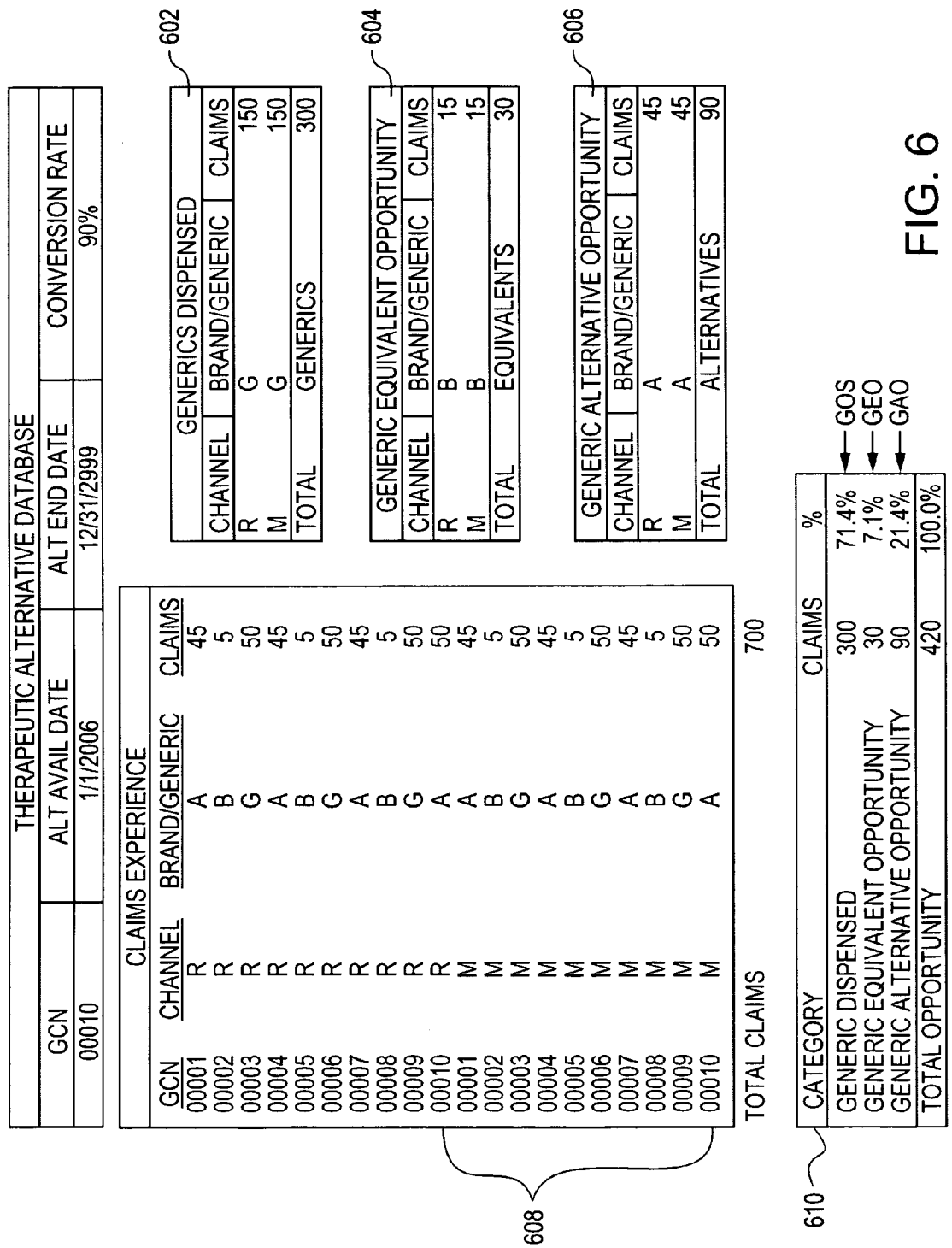
FIG. 6 illustratively depicts the calculation and identification of GOS, GEO, and GAO in accordance with some embodiments of the disclosed subject matter.

In some embodiments, the GOS can be calculated and displayed to a user. For example, referring to FIG. 6, a display indicating the GOS is illustratively depicted. The user's prescription claims database can be accessed, queries run, code numbers assigned, and generic data sets created per the process described in FIG. 5. Summary boxes 602, 604, 606 can indicate the sorted and/or filtered totals for Generics Dispensed, Generic Equivalent Opportunity, and Generic Alternative Opportunity.

In some instances, the generic alternative opportunity can be indicated to a user in the display. For example, the highlighted GCN 608 can represent the generic formulation that has been cross referenced with the Generic Alternative Database and identified as having a generic alternative opportunity.

Summary box 610 can capture the score calculations and define the total generic opportunity. For example, an additional 120 claims that could have been filled by either a generic equivalent (30) or a generic alternative (90) is displayed. For example, the 90 additional alternative claims can be a gross number and can be factored at a generic opportunity rate based on the criteria outlined out lined above regarding the therapeutic alternative database.

In some embodiments, a communication can be sent to the user regarding prescription drug uses that provides information regarding one or more generic alternatives. For example, a letter, email, phone call, or any other communication can be sent to prescription drug user informing them of a generic alternative.

Figure 7:
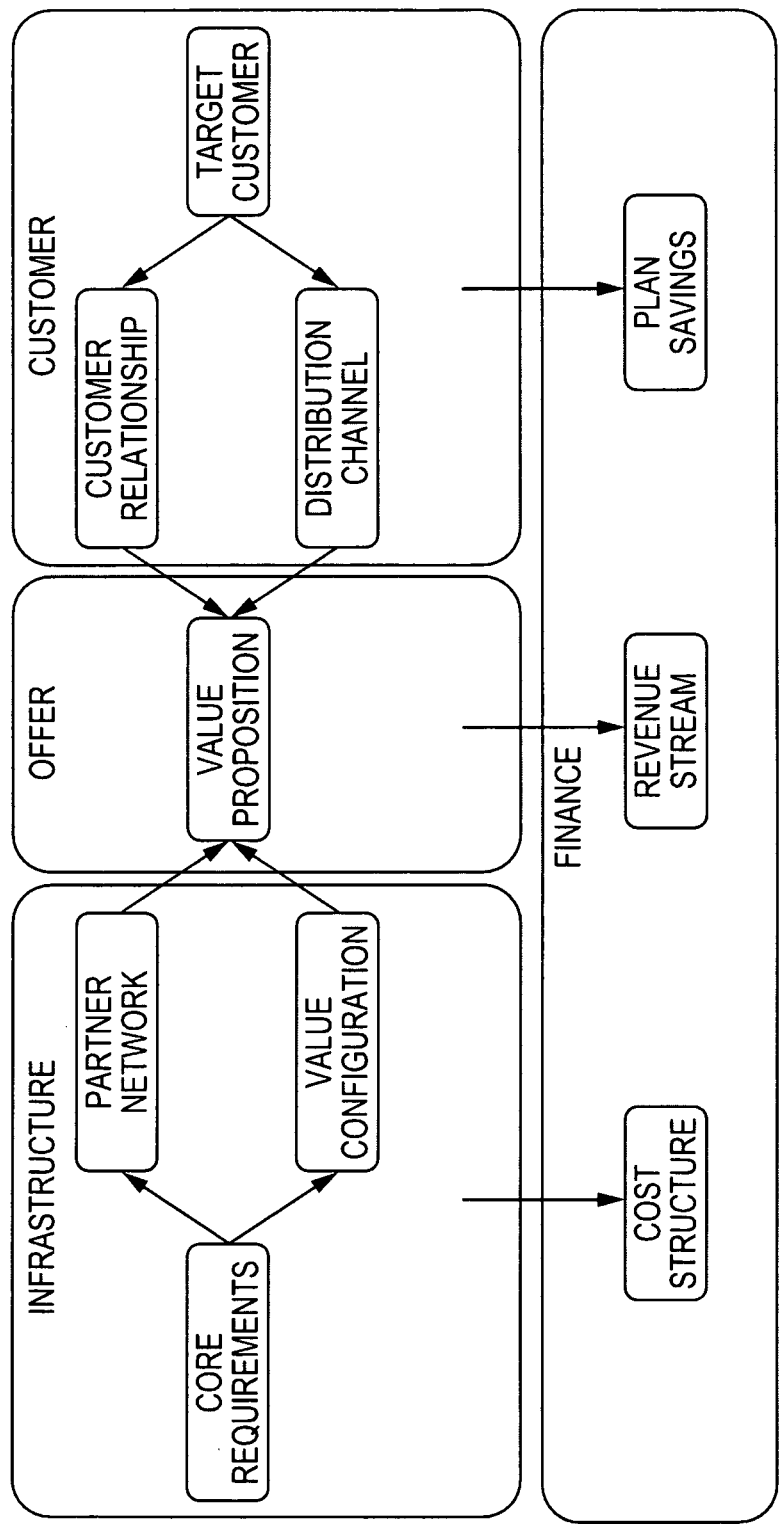
FIG. 7 illustratively depicts a business model for implementing GOS in accordance with some embodiments of the disclosed subject matter.

FIG. 7 illustratively depicts a business model for implementing GOS. For example, the business model can have, inter alia, four categories with subcategories: infrastructure, offer, customer, and/or finance. Each of the four categories can be modified, combined, or further separated without deviating from the scope of the invention.

The infrastructure can include core requirements, a partner network, and/or value configuration. The core requirements may include, but are not limited to, a therapeutic alternative list, conversion rates, Information Warehouse (IW) access and reporting, and/or financial modeling updates. The partner network can include, but is not limited to, a channel and generic strategy, Department of Medical and Analytical Affairs (DMAA), formulary, expert advisor, marketing and personal relations, consultant services, and/or an account management. The value configuration can include, but is not limited to, establishing generic opportunity, attaining maximum conversion, reporting and guaranteeing the metric, and/or modeling enhancements.

The offer can include a value proposition. The value proposition can include, but is not limited to, increasing user awareness on therapeutic alternative generics, showcasing programs and products designed to improve GOS and plan savings, and/or creating new market measurements that define a user specific opportunity.

The customer category can include, but is not limited to, customer relationship, target customer, and/or distribution channel. The customer relationship sub-category can include, but is not limited to, establishing a consultative relationship, providing lowest net cost alternatives, and/or strong generic messaging. The distribution channel can include, but is not limited to, account teams, drug trend reports, consultants, and/or senior leadership. The target customer can include, but is not limited to, existing users, prospective users, and/or consultants.

The finance category can include, but is not limited to, at least, three elements and/or subcategories: cost structure, revenue stream, and/or plan savings. The cost structure relating to the infrastructure can include, but is not limited to, the resources to maintain a therapeutic alternative database and generic opportunity rates, creating indicator on the IW to identify single source brands and their therapeutic alternative, and/or updating all modeling tools to include claim conversion opportunity. Revenue stream can include, but is not limited to, increasing use of generics and mail utilization and upsell of products and/or programs. Plan savings can include, but is not limited to, increasing plan usage of the lowest cost alternative and/or channel.

Figure 8:
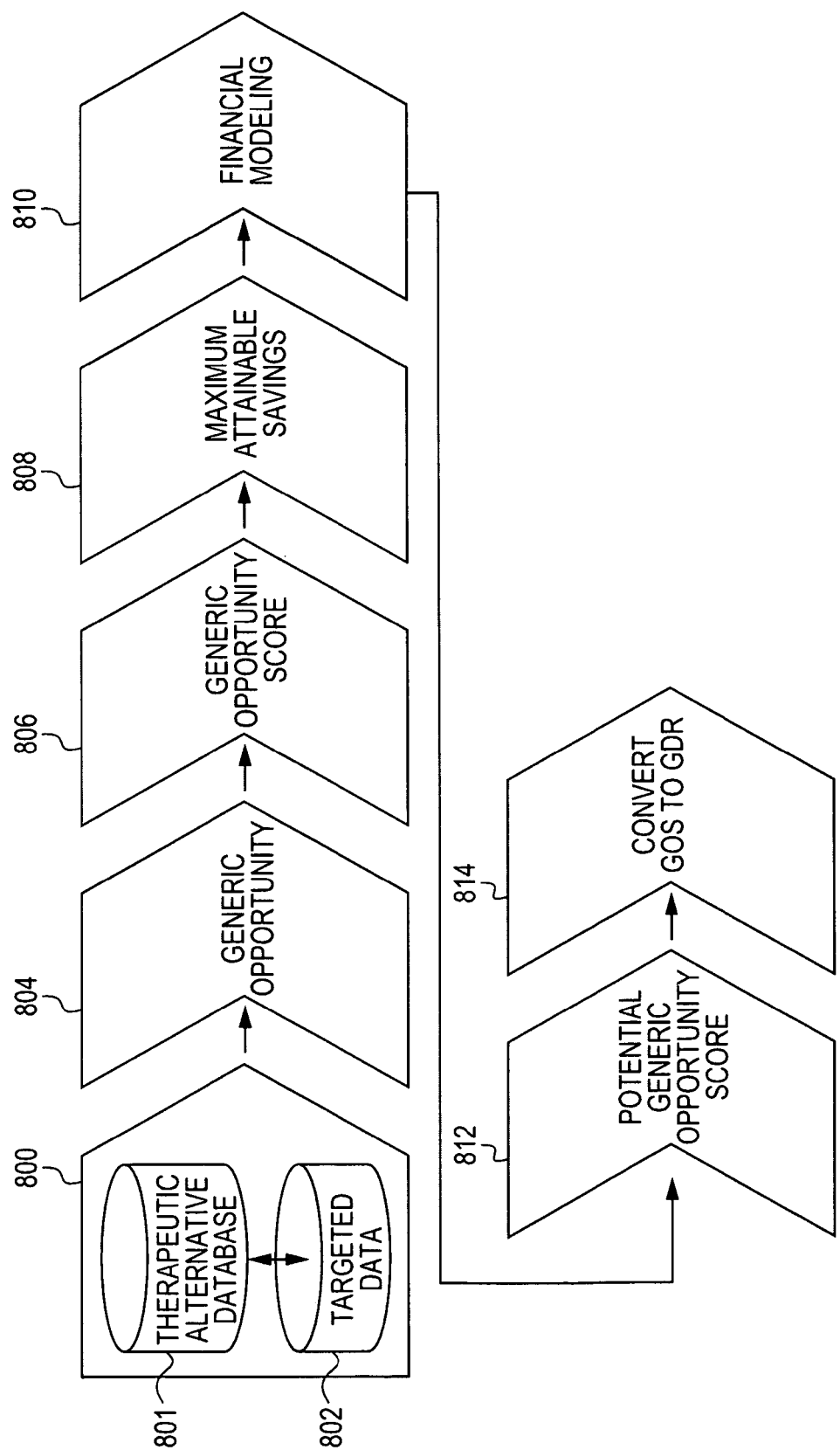
FIG. 8 illustratively displays a flow chart for GOS in accordance with some embodiments of the disclosed subject matter.

FIG. 8 illustratively displays a flow chart for GOS. Initially, at 800, the therapeutic alternative database 801 and targeted data 802 (e.g., a group of claims for a specific time period being evaluated for generic dispensing performance) can be cross referenced with each other. At generic opportunity 804, the total generic opportunity can be calculated by, for example, the sum of generics, therapeutic equivalents, and therapeutic alternatives. At generic opportunity score 806, the total generics dispensed over the generic opportunity can be calculated. At maximum attainable savings 808, using, for example, clinically viable conversion rates from the therapeutic alternative database maximum savings can be estimated. At financial modeling 810, using existing standard program models for generic uptake, the generic uptake can be determined. At potential generic score 812, the program performance results from financial modeling can be added to current GOS to determine the generic potential. At convert GOS to GDR 814, the generic potential can be converted back to an established metric such as GDR.

In some embodiments, drug model information from a therapeutic alternative database and a claims experience (e.g., any variation of grouping claims data for any given time period) can be communicated to each other. The therapeutic alternative database can include therapeutic drug alternatives and practical generic opportunity rate limits. Information from the drug model can be communicated to determine the generic opportunity and generic opportunity score (GOS). It will be understood that the Generic Opportunity can be the GEO and GAO. Information (e.g., the generic opportunity and generic opportunity score) from the GOS can be communicated to a first financial model and/or a second financial model. The first financial model can determine the GOS Score and possible savings if 100% conversion to the generic alternative opportunities were to occur. For example, the first financial model can be the cost of the brand claim less the cost of the generic alternative claim. The second financial model can determine the effect certain generic programs have on the GOS Score and the possible savings. Information from the first financial model, second financial model, and GOS can be communicated between each of the first financial model, the second financial model, and the GOS.

In some embodiments GOS calculations can be based on any of the following criteria: claims, days of therapy, quantity filled, Average Wholesale Price (AWP), ingredient cost, gross cost, patient payment (e.g., copay, deductible, and penalties), plan cost, net cost, and/or any other criteria deemed suitable. Further, in some embodiments GOS can be evaluated at various levels of detail, for example, user, Therapeutic Resource Center (TRC), various levels of therapeutic chapters, patient, rational med incorporation of medical data, specialty, disease state, and/or any other level deemed suitable.

Figure 9:
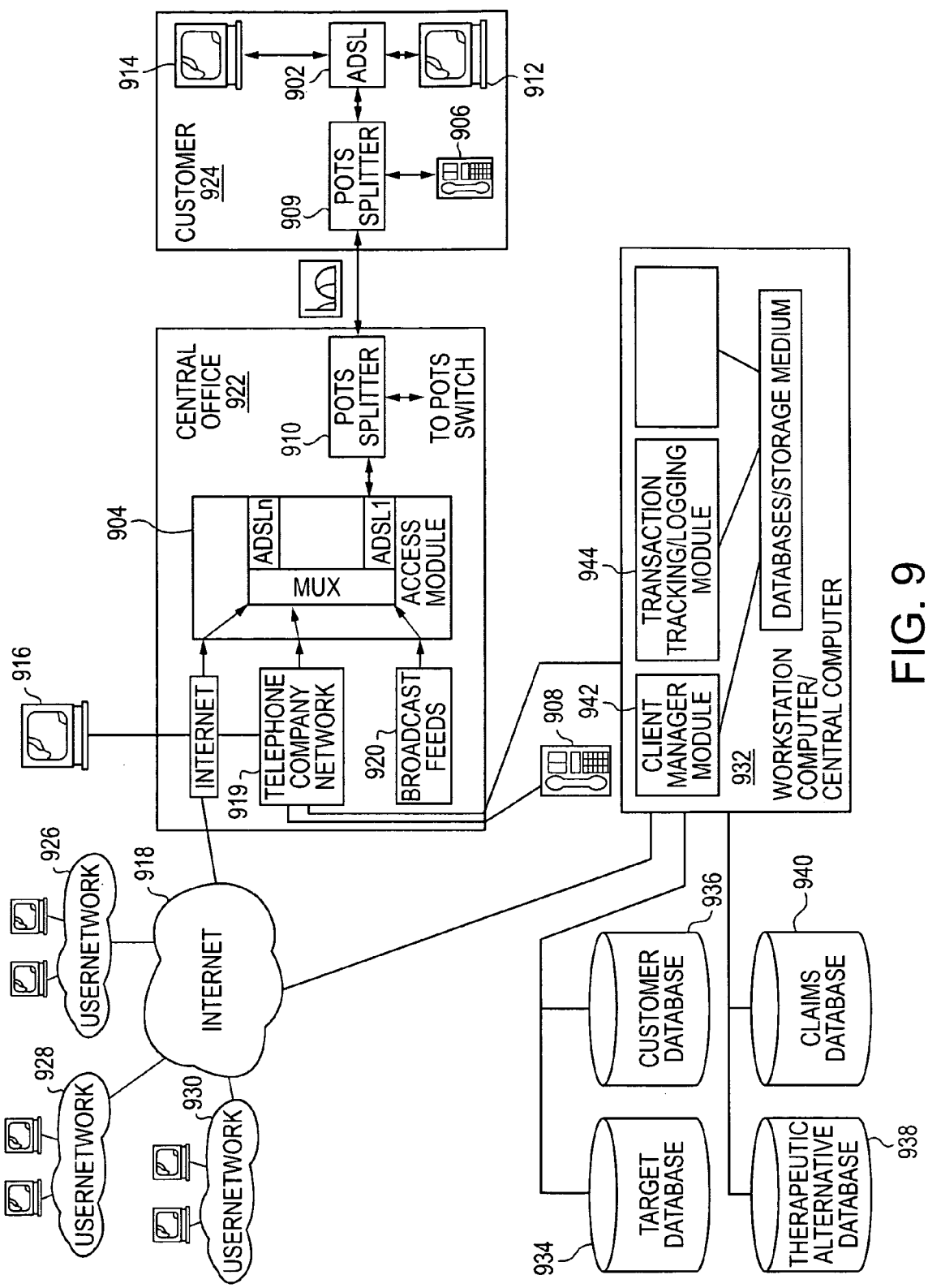
FIG. 9 illustratively displays the architecture of the combined Internet, POTS (plain, old, telephone service), and ADSL (asymmetric, digital, subscriber line) for use in accordance with some embodiments of the disclosed subject matter.

FIG. 9 is an illustration of the architecture of the combined Internet, POTS (plain, old, telephone service), and ADSL (asymmetric, digital, subscriber line) for use in accordance with the principles of the present invention (e.g., accessing the Web site for finding generic drugs). Furthermore, it is to be understood that the use of the Internet, ADSL, and POTS are for exemplary reasons only and that any suitable communications network may be substituted without departing from the principles of the present invention. This particular example is briefly discussed below.

In FIG. 9, to preserve POTS and to prevent a fault in the ADSL equipment 902, 904 from compromising analog voice traffic 906, 908 the voice part of the spectrum (the lowest 4 kHz) is separated from the rest by a passive filter, called a POTS splitter 909, 1010. The rest of the available bandwidth—from about 10 kHz to 1 MHz—carries data at rates up to 6 bits per second for every hertz of bandwidth from data equipment 912, 914, and 916. The ADSL equipment 904 then has access to a number of destinations including significantly the Internet 918 or other data communications networks, and other destinations 919, 920.

To exploit the higher frequencies, ADSL makes use of advanced modulation techniques, of which the best known is the discrete multitone (DMT) technology. As its name implies, ADSL transmits data asymmetrically—at different rates upstream toward the central office 922 and downstream toward the subscriber 924.

Cable television services are providing analogous Internet service to PC users over their TV cable systems by means of special cable modems. Such modems are capable of transmitting up to 30 Mb/s over hybrid fiber/coax system, which use fiber to bring signals to a neighborhood and coax to distribute it to individual subscribers.

Cable modems come in many forms. Most create a downstream data stream out of one of the 6-MHz TV channels that occupy spectrum above 50 MHz (and more likely 550 MHz) and carve an upstream channel out of the 5-50-MHz band, which is currently unused. Using 64-state quadrature amplitude modulation (64 QAM), a downstream channel can realistically transmit about 30 Mb/s (the oft-quoted lower speed of 10 Mb/s refers to PC rates associated with Ethernet connections). Upstream rates differ considerably from vendor to vendor, but good hybrid fiber/coax systems can deliver upstream speeds of a few megabits per second. Thus, like ADSL, cable modems transmit much more information downstream than upstream. Then Internet architecture 918 and ADSL architecture 902, 904 may also be combined with, for example, user networks 926, 928, and 930.

In accordance with the principles of the present invention, in one example, a main computing server implementing the process of the invention may be located on one or more computing nodes or terminals (e.g., on user networks 926, 928, and 930 or system 932). Then, various users may interface with the main server via, for instance, the ADSL equipment discussed above, and access the information and processes of the present invention from remotely located PCs. As illustrated in this embodiment, users may access, use or interact with the computer assisted program in computer system 932 via various access methods. Databases 934, 936, 938, 940, and 932 are accessible via, for example computer system 932 and may be used in conjunction with user manager module 942, tracking module 944, for the various functions described above.

Figure 10:
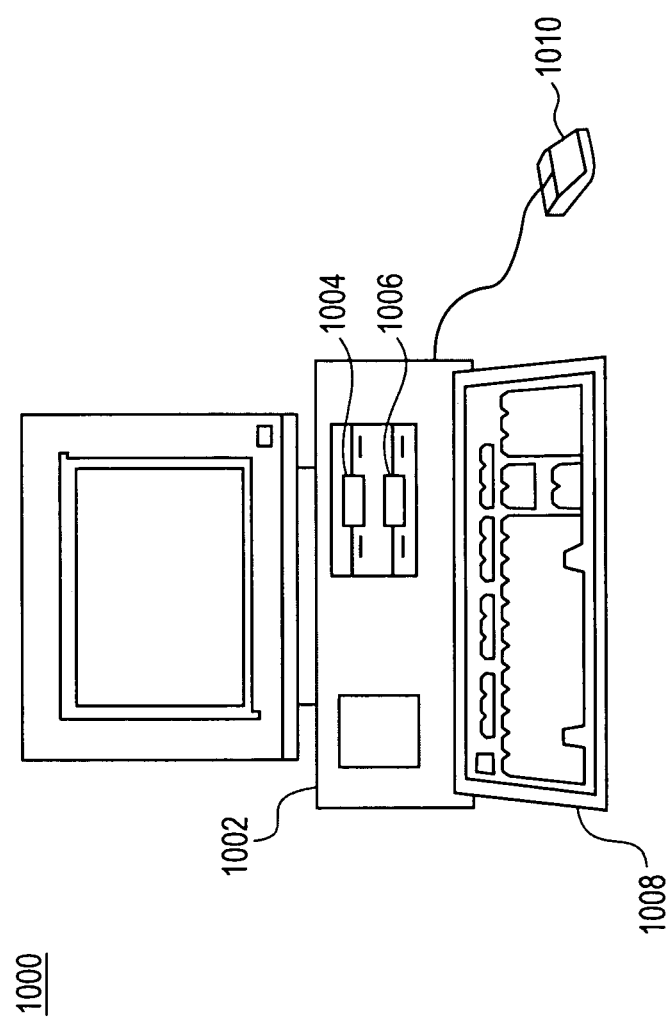
FIG. 10 illustratively displays a computer system for use in accordance with some embodiments of the disclosed subject matter.

Viewed externally in FIG. 10, a computer system (e.g., a user interface) designated by reference numeral 1000 has a computer 1002 having disk drives 1004 and 1006. Disk drive indications 1004 and 1006 are merely symbolic of a number of disk drives which might be accommodated by the computer system. Typically, these would include a floppy disk drive 1004, a hard disk drive (not shown externally) and a CD ROM indicated by slot 1006. The number and type of drives vary, typically with different computer configurations. Disk drives 1004 and 1006 are in fact optional, and for space considerations, are easily omitted from the computer system used in conjunction with the production process/apparatus described herein.

The computer system also has an optional display upon which information screens may be displayed. In some situations, a keyboard 1008 and a mouse 1010 are provided as input devices through which a user's actions may be inputted, thus allowing input to interface with the central processing unit 1002. Then again, for enhanced portability, the keyboard 1008 is either a limited function keyboard or omitted in its entirety. In addition, mouse 1010 optionally is a touch pad control device, or a track ball device, or even omitted in its entirety as well, and similarly may be used to input a user's selections. In addition, the computer system also optionally includes at least one infrared transmitter and/or infrared received for either transmitting and/or receiving infrared signals, as described below.

Figure 11:
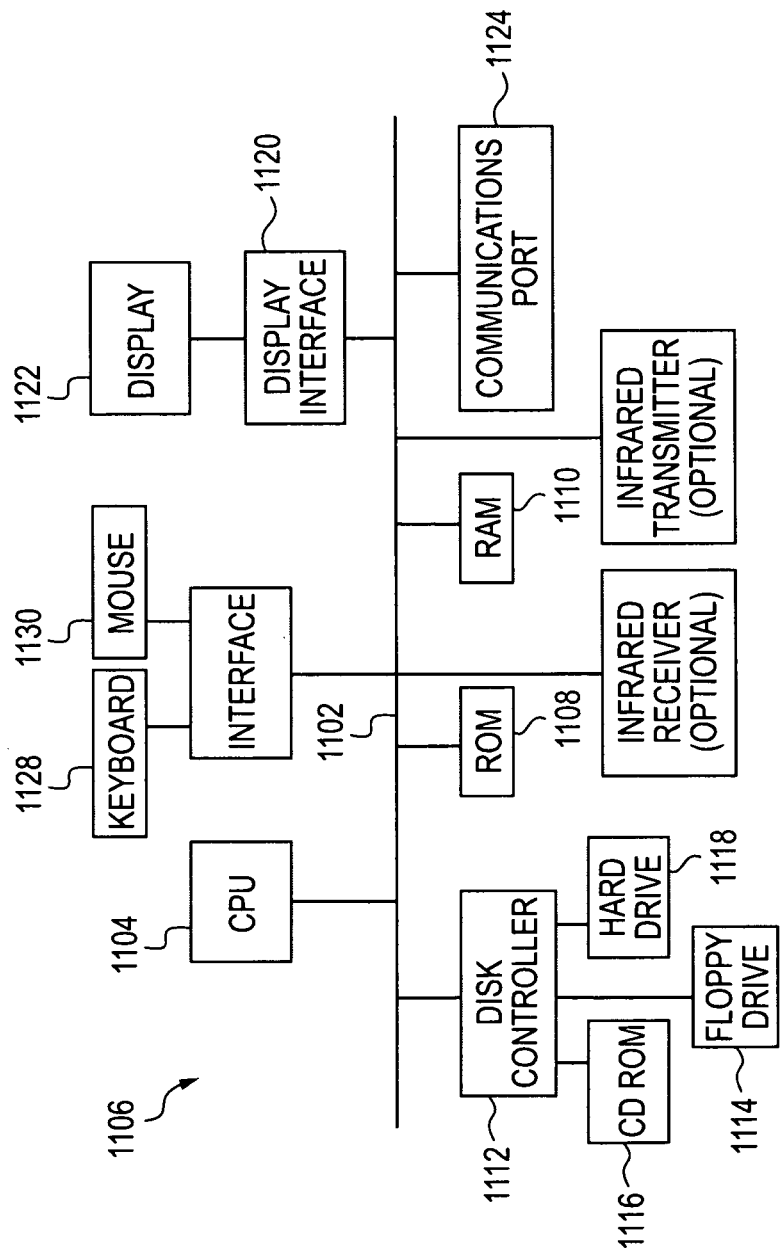
FIG. 11 illustratively displays a block diagram of one example of the internal hardware configured to perform a server function for the Web pages described in accordance with some embodiments of the disclosed subject matter.

FIG. 11 illustrates a block diagram of one example of the internal hardware configured to perform a server function for the Web pages described above. A bus 1102 serves as the main information highway interconnecting various components therein. CPU 1104 is the central processing unit of the internal hardware 1106, performing calculations and logic operations required to execute the control/operation processes of the present invention as well as other programs. Read only memory (ROM) 1108 and random access memory (RAM) 1110 constitute the main memory of the internal hardware 1106. Disk controller 1112 interfaces one or more disk drives to the system bus 1102. These disk drives are, for example, floppy disk drives, or CD ROM or DVD (digital video disks) drives, or internal or external hard drives. These various disk drives and disk controllers are optional devices.

A display interface 1120 interfaces display 1122 and permits information from the bus 1102 to be displayed on display 1122. Display 1122 may be used in displaying various Web pages. Communications with external devices such as the other components of the system described above, occur utilizing, for example, communication port 1124. Optical fibers and/or electrical cables and/or conductors and/or optical communication (e.g., infrared, and the like) and/or wireless communication (e.g., radio frequency (RF), and the like) can be used as the transport medium between the external devices and communication port 1124. Peripheral interface 1126 interfaces the keyboard 1128 and mouse 1130, permitting input data to be transmitted to bus 1102. In addition to these components, the internal hardware 1106 also optionally includes an infrared transmitter and/or infrared receiver. Infrared transmitters are optionally utilized when the computer system is used in conjunction with one or more of the processing components/stations/modules that transmits/receives data via infrared signal transmission. Instead of utilizing an infrared transmitter or infrared receiver, the computer system may also optionally use a low power radio transmitter and/or a low power radio receiver. The low power radio transmitter transmits the signal for reception by components of the production process, and receives signals from the components via the low power radio receiver. The low power radio transmitter and/or receiver are standard devices in industry.

Although the server in FIG. 11 is illustrated having a single processor, a single hard disk drive and a single local memory, the analyzer is optionally suitably equipped with any multitude or combination of processors or storage devices. For example, the computer may be replaced by, or combined with, any suitable processing system operative in accordance with the principles of embodiments of the present invention, including sophisticated calculators, and hand-held, laptop/notebook, mini, mainframe and super computers, as well as processing system network combinations of the same.

In general, it should be emphasized that the various components of embodiments of the present invention can be implemented in hardware, software or a combination thereof. In such embodiments, the various components and steps would be implemented in hardware and/or software to perform the functions of embodiments of the present invention. Any presently available or future developed computer software language and/or hardware components can be employed in such embodiments of the present invention. For example, at least some of the functionality mentioned above could be implemented using Visual Basic, C, C++, or any assembly language appropriate in view of the processor(s) being used. It could also be written in an interpretive environment such as Java and transported to multiple destinations to various users.

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

What is claimed is:

1. A method comprising:
    determining, on a processor, a number of generic prescriptions dispensed from claims data;
    determining, on the processor, a number of brand name prescription drugs dispensed with a generic equivalent from the claims data, the generic equivalent of a brand name prescription drug being a drug produced after expiration of a patent on the brand name prescription drug that includes the same active ingredients as the prescription drug but is sold under a different brand name through a different manufacturer than the manufacturer of the band name prescription drug;
    determining, on the processor, a number of brand name prescription drugs dispensed with a generic alternative from the claims data, the generic alternative used to treat a same condition as the brand name prescription drug but including different chemicals than those included in the brand name prescription drug;
    calculating, on the processor, a ratio of the number of generic prescriptions dispensed to a combination of the number of generic prescriptions dispensed, the number of brand name prescription drugs with a generic equivalent, and the number of brand name prescription drugs dispensed with a generic alternative;
    determining, on the processor, a total dollar spent on prescription claims for generic prescriptions dispensed and brand prescriptions dispensed included among the claims data;
    applying, on the processor, the calculated ratio to the total dollar spent to generate a generic equivalent portion from the total dollar spent; and
    determining a potential amount of savings associated with generic drug usage based on the claims data and generation of the generic equivalent portion.

2. The method of claim 1, further comprising:
    sorting the claims data into groups of generic prescriptions dispensed, brand prescription drugs with generic equivalents, and brand prescription drugs with generic alternative data into three groups of data
    wherein sorting of the claims data is performed prior to determination of the number of generic prescriptions dispensed, determination of the number of brand name prescriptions dispensed with a generic equivalent, and determination of the number of brand name prescriptions dispensed with a generic alternative.

3. The method of claim 1, further comprising:
    generating price differential data for each brand name prescription among the claims data that could have been fulfilled by at least one of a generic equivalent or clinically-appropriate generic alternative.

4. The method of claim 1, further comprising:
    generating a message to a recipient of a particular brand name prescription drug regarding a particular generic equivalent to the particular brand name prescription drug.

5. The method of claim 1, wherein the number of generic prescriptions dispensed from claims data included a number of the generic maintenance prescription drugs dispensed, the number of brand name prescription drugs dispensed with a generic equivalent from the claims data include the number of brand name maintenance prescription drugs dispensed with a generic equivalent, and the number of brand name prescription drugs dispensed with a generic alternative from the claims data include the number of brand name maintenance prescription drugs dispensed with a generic alternative, and
    wherein calculating the ratio includes calculating the number of generic maintenance prescription drugs dispensed to a combination of the number of generic maintenance prescription drugs dispenses, the number of brand name maintenance prescription drugs with a generic equivalent, and the number of brand name maintenance prescription drugs dispensed with a generic alternative.

6. The method of claim 1, wherein the number of generic prescriptions dispensed from claims data included a number of the generic acute prescription drugs dispensed, the number of brand name prescription drugs dispensed with a generic equivalent from the claims data include the number of brand name acute prescription drugs dispensed with a generic equivalent, and the number of brand name prescription drugs dispensed with a generic alternative from the claims data include the number of brand name acute prescription drugs dispensed with a generic alternative, and
    wherein calculating the ratio includes calculating the number of generic acute prescription drugs dispensed to a combination of the number of generic acute prescription drugs dispenses, the number of brand name acute prescription drugs with a generic equivalent, and the number of brand name acute prescription drugs dispensed with a generic alternative.

7. A non-transitory machine-readable medium comprising instructions, which when executed by one or more processors, cause the one or more processors to perform the following operations:
    determine a number of generic prescriptions dispensed from claims data; determine a number of brand name prescription drugs dispensed with a generic equivalent from the claims data, the generic equivalent of a brand name prescription drug being a drug produced after expiration of a patent on the brand name prescription drug that includes the same active ingredients as the prescription drug but is sold under a different brand name through a different manufacturer than the manufacturer of the band name prescription drug;

determine a number of brand name prescription drugs dispensed with a generic alternative from the claims data, the generic alternative used to treat a same condition as the brand name prescription drug but including different chemicals than those included in the brand name prescription drug;

calculate a ratio of the number of generic prescriptions dispensed to a combination of the number of generic prescriptions dispensed, the number of brand name prescription drugs with a generic equivalent, and the number of brand name prescription drugs dispensed with a generic alternative;

determine a total dollar spent on prescription claims for generic prescriptions dispensed and brand prescriptions dispensed included among the claims data;

apply the calculated ratio to the total dollar spent to generate a generic equivalent portion from the total dollar spent; and determine a potential amount of savings associated with generic drug usage based on the claims data and generation of the generic equivalent portion.

* * * * *